US011141054B2

(12) United States Patent
Nakamura

(10) Patent No.: US 11,141,054 B2
(45) Date of Patent: Oct. 12, 2021

(54) ENDOSCOPE AND ENDOSCOPE APPARATUS

(71) Applicant: OLYMPUS CORPORATION, Tokyo (JP)

(72) Inventor: Sho Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 382 days.

(21) Appl. No.: 16/154,798

(22) Filed: Oct. 9, 2018

(65) Prior Publication Data

US 2019/0038121 A1    Feb. 7, 2019

Related U.S. Application Data

(63) Continuation of application No. PCT/JP2016/067434, filed on Jun. 10, 2016.

(51) Int. Cl.
| | | |
|---|---|---|
| *A61B 1/12* | (2006.01) | |
| *A61B 1/00* | (2006.01) | |
| *A61B 1/05* | (2006.01) | |
| *A61B 1/045* | (2006.01) | |
| *A61B 1/06* | (2006.01) | |
| *A61B 1/07* | (2006.01) | |

(52) U.S. Cl.
CPC .......... *A61B 1/128* (2013.01); *A61B 1/00004* (2013.01); *A61B 1/00006* (2013.01); *A61B 1/00009* (2013.01); *A61B 1/00188* (2013.01); *A61B 1/045* (2013.01); *A61B 1/05* (2013.01); *A61B 1/051* (2013.01); *A61B 1/0661* (2013.01); *A61B 1/0669* (2013.01); *A61B 1/0684* (2013.01); *A61B 1/07* (2013.01)

(58) Field of Classification Search
CPC . A61B 1/128; A61B 1/00009; A61B 1/00188; A61B 1/05; A61B 1/0669; A61B 1/00006; A61B 1/00004; A61B 1/045; A61B 1/051; A61B 1/0684; A61B 1/07; A61B 1/0661; G01R 33/12; G01R 33/15; G01R 11/185; G01R 19/32; G01R 33/07; G01R 33/09; G01R 33/02; G01R 19/02
USPC ......................................................... 600/103
See application file for complete search history.

(56) References Cited

U.S. PATENT DOCUMENTS 4,371,837 A * 2/1983 Sieverin ................. G01R 33/07
324/225

FOREIGN PATENT DOCUMENTS

| CN | 101169341 A * | 4/2008 |
|---|---|---|
| CN | 101169341 A | 4/2008 |

(Continued)

OTHER PUBLICATIONS

International Search Report dated Aug. 30, 2016 issued in PCT/JP2016/067434.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope includes a sensor, and a temperature compensation circuit configured to perform temperature compensation of an output signal of the sensor, in a distal end portion. The temperature compensation circuit includes a differential amplifying section configured to amplify an output signal of the sensor, and a temperature sensing section in which a resistance is connected in series to a parallel connection portion of a temperature sensing element and a resistance.

8 Claims, 6 Drawing Sheets

(56) References Cited

FOREIGN PATENT DOCUMENTS

| | | | |
|---|---|---|---|
| CN | 101476921 A | 7/2009 | |
| JP | 2008-252906 A | 10/2008 | |
| JP | 2012-050509 A | 3/2012 | |
| JP | 2014-131531 A | 7/2014 | |
| JP | 2014150924 A * | 8/2014 | |
| WO | WO-2015015942 A1 * | 2/2015 | ............. A61B 1/018 |

* cited by examiner

ENDOSCOPE AND ENDOSCOPE APPARATUS

CROSS REFERENCE TO RELATED APPLICATION

This application is a continuation application of PCT/JP2016/067434 filed on Jun. 10, 2016, the entire contents of which are incorporated herein by this reference.

BACKGROUND OF THE INVENTION

1. Field of the Invention

The present invention relates to an endoscope and an endoscope apparatus.

2. Description of the Related Art

Conventionally, an endoscope apparatus including an endoscope that picks up an image of an object inside a subject, a processor that generates an observation image of the object the image of which is picked up by the endoscope, and a monitor that displays an observation image generated by the processor has been widely used in a medical field, an industrial field and the like.

In the endoscope, various sensors are disposed, such as an image pickup device such as a CCD image sensor or a CMOS image sensor, and a magnetic coil for detecting an endoscope shape. Input and output signals of the various sensors are transmitted to a signal detection circuit disposed in a connector portion of the endoscope (that is, a connection portion to the processor) or the processor, through a long cable.

The various sensors as above have temperature dependency, so that it is necessary to perform temperature correction of the output signals in order to ensure precision of the output signals of the sensors. For example, Japanese Patent Application Laid-Open Publication No. 2008-252906 proposes an endoscope apparatus that is provided with a temperature sensor in the distal end portion of the endoscope, and removes dark current noise of a CCD in the temperature correction circuit provided in the processor based on a temperature change around the CCD.

SUMMARY OF THE INVENTION

An endoscope of one aspect of the present invention is an endoscope including a sensor, and a temperature compensation circuit configured to perform temperature compensation of an output signal of the sensor, in a distal end portion, wherein the temperature compensation circuit includes a differential amplifying section configured to amplify an output signal of the sensor, and a temperature sensing section in which a resistance is connected in series to a parallel connection portion of a temperature sensing element and a resistance.

Further, an endoscope apparatus of one aspect of the present invention includes a processor configured to be connected to the endoscope, wherein the endoscope includes a cable and a connector portion configured to be detachably connected to the processor, and the processor generates a reference voltage that is supplied to the differential amplifying section, and transmits the reference voltage through the connector portion and the cable.

Further, an endoscope apparatus of another aspect of the present invention includes a processor configured to be connected to the endoscope, wherein the endoscope includes a cable and a connector portion configured to be detachably connected to the processor, and the connector portion generates a reference voltage that is supplied to the differential amplifying section, and transmits the reference voltage through the cable.

DETAILED DESCRIPTION OF THE PREFERRED EMBODIMENTS

Embodiments of the present invention will be described below with reference to the drawings.

First Embodiment

Figure 1:
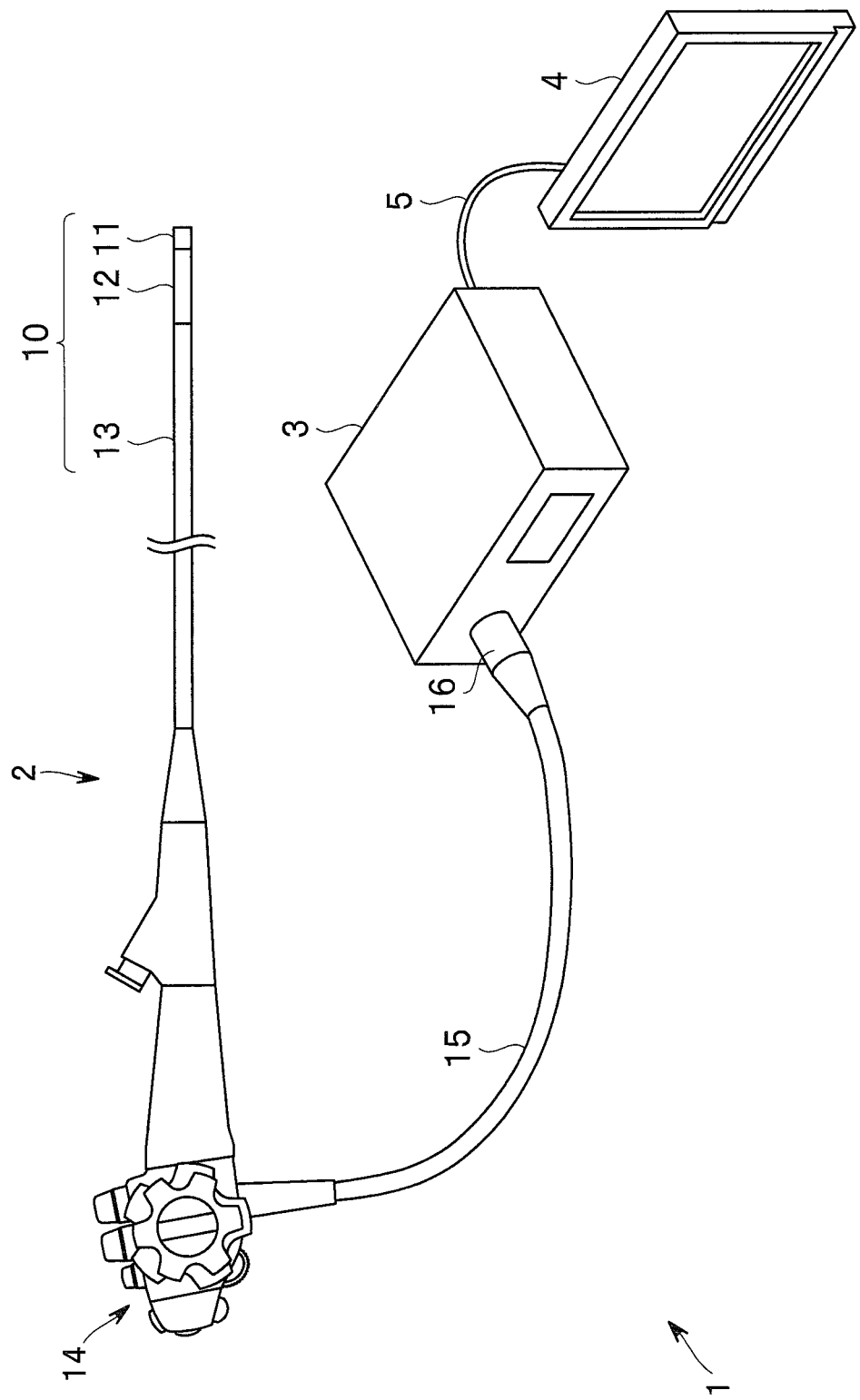
FIG. 1 is a configuration diagram illustrating a configuration of an endoscope apparatus according to a first embodiment.

FIG. 1 is a configuration diagram illustrating a configuration of an endoscope apparatus according to a first embodiment. As illustrated in FIG. 1, an endoscope apparatus 1 of the present embodiment is configured mainly by an endoscope 2, a processor 3 and a monitor 4. The processor 3 and the monitor 4 are electrically connected via a cable 5.

The endoscope 2 of the present embodiment has a configuration in which the endoscope 2 is capable of being introduced into a subject such as a human body and optically picks up an image of a predetermined observation site in the subject. Note that the subject into which the endoscope 2 is introduced may not only be a human body but other living bodies, or artificial objects such as a machine and a building.

The endoscope 2 is configured mainly by an insertion portion 10 configured to be inserted into a subject, an operation portion 14 located at a proximal end of the insertion portion 10, and a universal cable (hereinafter simply referred to as a cable) 15 extending from a side portion of the operation portion 14.

The insertion portion 10 is configured such that a distal end portion 11 placed at a distal end, a bendable bending portion 12 placed at a proximal end side of the distal end portion 11, and a flexible tube portion 13 having flexibility that is placed at a proximal end side of the bending portion 12 and connected to a distal end side of the operation portion 14 are connectively provided.

The operation portion 14 includes a vertically-bending operation knob configured to bend the bending portion 12 in a vertical direction, a laterally-bending operation knob configured to bend the bending portion 12 in a lateral direction, an air/water feeding button for performing air/water feeding, a suction button for performing suction, switches for executing various endoscope functions, and the like.

A connector portion 16 configured to be connected to the processor 3 is provided at a proximal end portion of the cable 15. The endoscope 2 is configured to be detachably connected to the processor 3 via the connector portion 16.

The processor 3 drives and controls a lens of an image pickup unit provided in the distal end portion 11 and described later. Further, the processor 3 applies predetermined video signal processing to an image pickup signal outputted from an image pickup device of the image pickup unit provided in the distal end portion 11 and described later, and generates a predetermined video signal to output the predetermined video signal to the monitor 4. That is, the processor 3 causes the monitor 4 to display an optical image (an endoscopic image) picked up by the image pickup device as a video.

Further, in the processor 3, a light source apparatus is integrally formed. That is, the processor 3 emits illuminating light emitted by a light source such as a halogen lamp or an LED to the subject from a distal end surface of the distal end portion 11 of the endoscope 2 via a light guide or the like inserted through the endoscope 2 and the processor 3.

Figure 2:
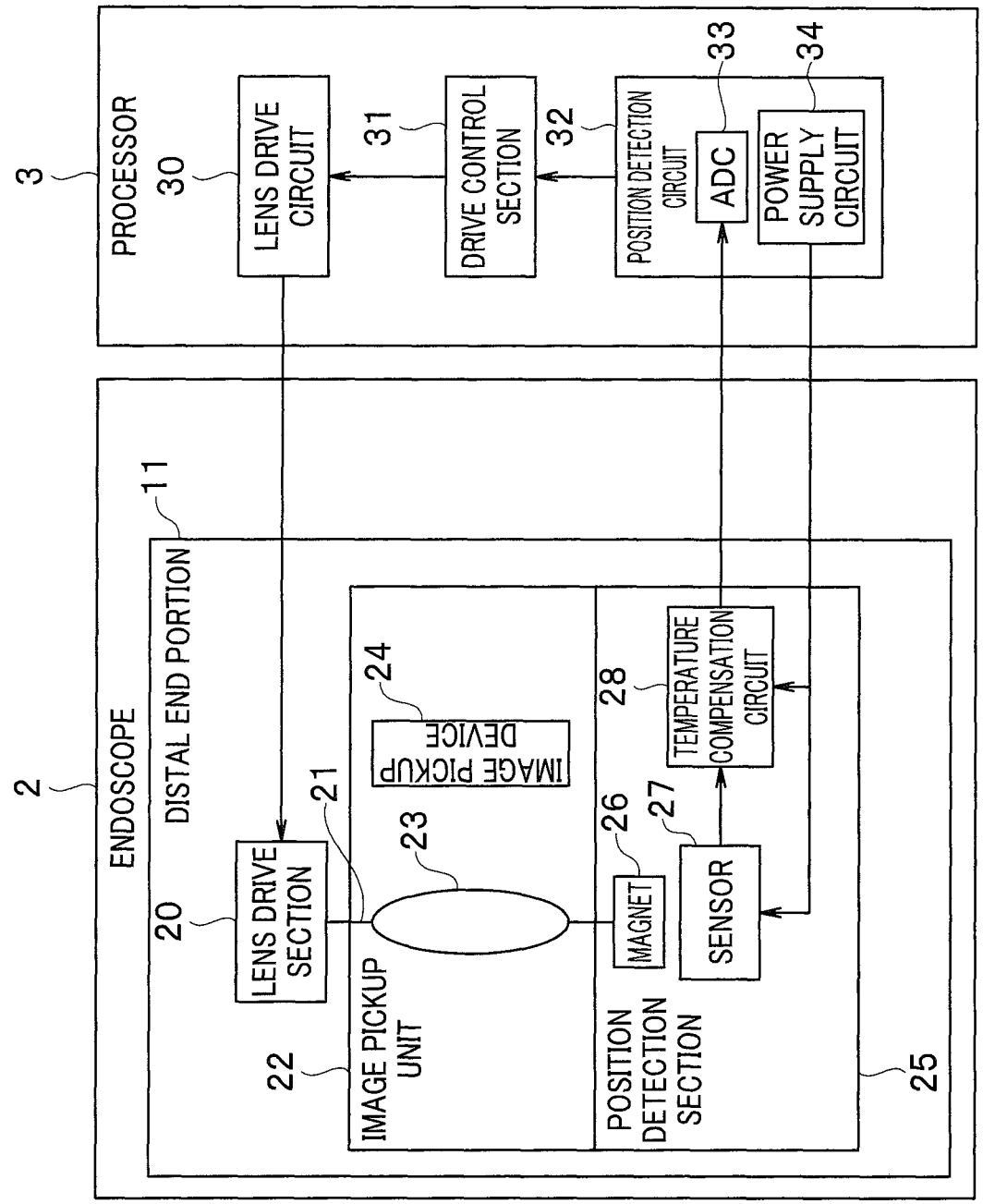
FIG. 2 is a configuration diagram for explaining detailed configurations of an endoscope and a processor.

FIG. 2 is a configuration diagram for explaining detailed configurations of the endoscope and the processor.

The distal end portion 11 of the endoscope 2 is configured by having a lens drive section 20, a lens frame 21, an image pickup unit 22 and a position detection section 25. The image pickup unit 22 is configured by having an objective lens 23 and an image pickup device 24. The position detection section 25 is configured by having a magnet 26, a sensor 27 and a differential amplifying section 28.

The processor 3 is configured by having a lens drive circuit 30, a drive control section 31 and a position detection circuit 32. The position detection circuit 32 is configured by having an analog digital converter (hereinafter referred to as ADC) 33 and a power supply circuit 34.

The lens drive section 20 causes the objective lens 23 held by a lens frame 21 to advance and retract in a longitudinal direction of the insertion portion 10 based on a current value from the lens drive circuit 30. As the lens drive section 20, for example, a voltage actuator, a motor or the like is used. The objective lens 23 is caused to advance and retract in the longitudinal direction of the insertion portion 10 by the lens drive section 20, whereby a focus position is changeable.

The objective lens 23 forms an optical image of the illuminated object. The image pickup device 24 is an image sensor such as a CCD or a CMOS, and has a light receiving surface disposed in an image forming position of the objective lens 23. The image pickup device 24 generates an image pickup signal by picking up the optical image of the object, and outputs the generated image pickup signal to the processor 3 through a signal line (not illustrated) incorporated in the endoscope 2.

The processor 3 includes a video signal processing circuit (not illustrated) configured to apply predetermined video signal processing to the image pickup signal outputted from the image pickup device 24, and applies the predetermined video signal processing to the image pickup signal to generate a predetermined video signal. The processor 3 outputs the generated predetermined video signal to the monitor 4, and thereby causes the monitor 4 to display the optical image (the endoscopic image) picked up by the image pickup device as a video as described above.

Further, in the lens frame 21, the magnet 26 is disposed. The sensor 27 detects a position of the magnet 26 in accordance with the current from the power supply circuit 34 of the position detection circuit 32 of the processor 3, and outputs a signal to the temperature compensation circuit 28. The temperature compensation circuit 28 performs temperature compensation to the output signal of the sensor 27, and outputs the signal to the ADC 33 of the position detection circuit 32 of the processor 3. Note that a detailed configuration of the temperature compensation circuit 28 will be described later. The power supply circuit 34 generates a power supply of the sensor 27 and the temperature compensation circuit 28, and outputs the power supply to the sensor 27 and the temperature compensation circuit 28.

The ADC 33 converts an analog signal from the temperature compensation circuit 28 into a digital signal, and outputs the digital signal to the drive control section 31. The drive control section 31 determines a current value to be passed to the lens drive section 20 so that the position of the objective lens 23 becomes a desired position, and outputs information on the determined current value to the lens drive circuit 30.

The lens drive circuit 30 is a driver circuit that passes a current to the lens drive section 20. The lens drive circuit 30 outputs the current value determined by the drive control section 31 to the lens drive section 20 in accordance with the information on the current value from the drive control section 31.

Figure 3:
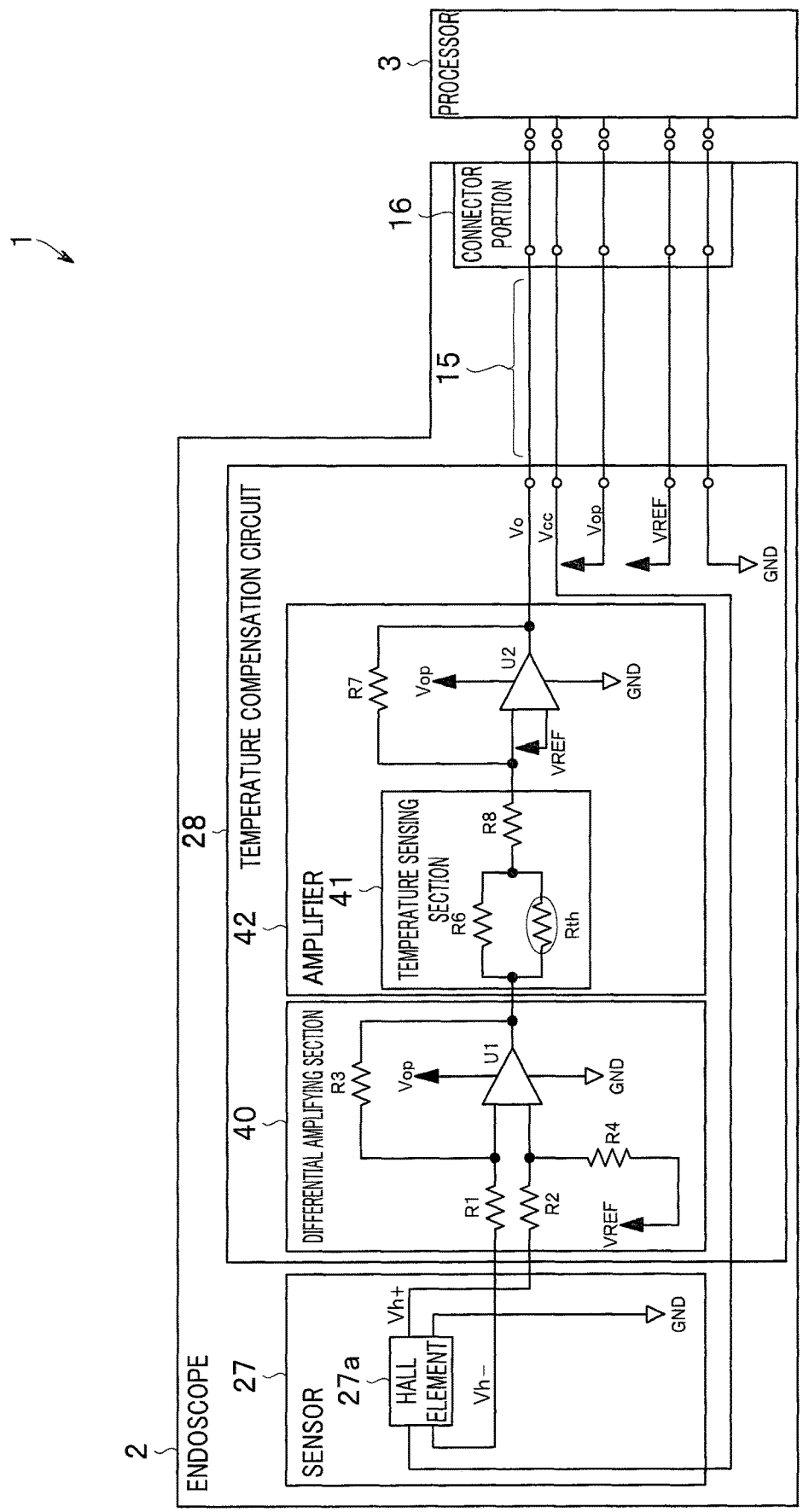
FIG. 3 is a diagram illustrating detailed configurations of a sensor and a temperature compensation circuit.

FIG. 3 is a diagram illustrating detailed configurations of the sensor and the temperature compensation circuit.

In the present embodiment, the sensor 27 that detects the position of the magnet 26 is configured by a Hall element 27a configured to detect a magnetic field. The Hall element 27a has two input terminals and two output terminals. Note that the sensor 27 may be not only the Hall element 27a but a magnetoresistive element, for example.

The temperature compensation circuit 28 is configured by having a differential amplifying section 40 that differentially amplifies an output signal from the Hall element 27a, and an amplifier 42 configured to invert and amplify the differentially amplified signal. The differential amplifying section 40 is connected to an input section of the amplifier 42. The amplifier 42 has a temperature sensing section 41.

The differential amplifying section 40 is configured by resistances R1 to R4, and an operational amplifier U1. The operational amplifier U1 is configured by including a non-inverting input terminal, an inverting input terminal and an output terminal. The power supply circuit 34 of the processor 3 generates power supply voltages of GND, VREF, Vop and Vcc, and supplies the power supply voltages to the sensor 27 and the temperature compensation circuit 28 through the connector portion 16 and the cable 15.

The endoscope apparatus 1 of the present embodiment generates a reference voltage VREF to be supplied to the differential amplifying section 40 and the amplifier 42 of the endoscope 2 by the power supply circuit 34 of the processor 3, and transmits the reference voltage VREF to the endoscope 2. Substantially no current flows in the cable 15 through which the reference voltage VREF is transmitted, so that a fluctuation of the voltage after amplification of the output signal from the Hall element 27a can be significantly suppressed. The fluctuation of the voltage after amplification of the output signal from the Hall element 27a is caused by a variation according to use environment of the resistances of the cable 15 and the connector portion 16 that connect the endoscope 2 and the processor 3. As a result, the endoscope 2 can perform temperature compensation with high precision.

A power supply Vcc from the processor 3 is connected to one of the input terminals of the Hall element 27a, and a ground GND from the processor 3 is connected to the other input terminal. One of the output terminals of the Hall element 27a is connected to the inverting input terminal of the operational amplifier U1 via the resistance R1. Further, the other output terminal of the Hall element 27a is connected to the noninverting input terminal of the operational amplifier U1 via the resistance R2. The reference voltage VREF is connected to the noninverting input terminal of the operational amplifier U1 via a resistance R4.

An electric potential outputted from the output terminal of the operational amplifier U1 is inputted to the inverting input terminal via the resistance R3. Further, the electric potential outputted from the operational amplifier U1 is inputted to the temperature sensing section 41.

The temperature sensing section 41 is configured by a resistance R8 connected in series to a parallel connection portion of a temperature sensing element Rth and a resistance R6. The temperature sensing element Rth is, for example, a chip type NTC (negative temperature coefficient) thermistor having a negative temperature characteristic, and decreases in resistance value when the temperature increases. The NTC thermistor is an element rather small in size among temperature sensing elements. Consequently, in the present embodiment, a circuit area of the temperature compensation circuit 28 can be decreased by using an NTC thermistor as the temperature sensing element Rth. As a result, the endoscope 2 can perform temperature compensation in a small space of the distal end portion 11.

Note that the temperature sensing element Rth is not limited to the NTC thermistor, but a PTC (positive temperature coefficient) thermistor or a CTR (critical temperature resistor) thermistor may be used in accordance with temperature dependency or the like of the sensor 27.

Figure 4:
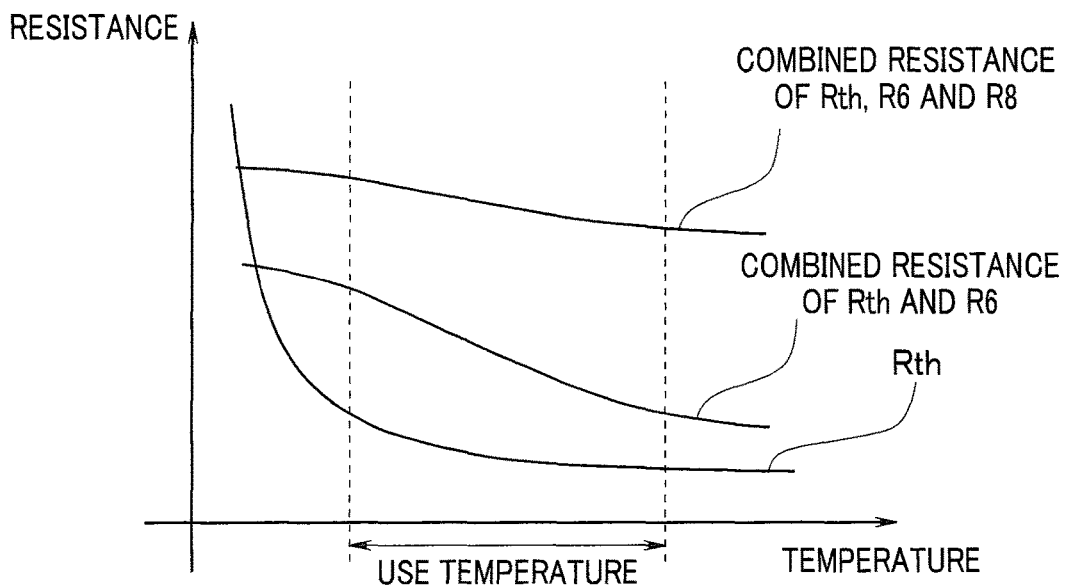
FIG. 4 is a diagram for explaining a relationship between a temperature and a combined resistance of a temperature sensing section 41 including a temperature sensing element Rth that is an NTC thermistor.

Here, a relationship between the temperature and the combined resistance of the temperature sensing section 41 including the temperature sensing element Rth that is an NTC thermistor will be described. FIG. 4 is a diagram for explaining the relationship between the temperature and the combined resistance of the temperature sensing section 41 including the temperature sensing element Rth that is an NTC thermistor.

The temperature sensing element Rth is an NTC thermistor, and as the temperature increases, the resistance decreases exponentially as illustrated in FIG. 4. The combined resistance of the temperature sensing element Rth and the resistance R6 which are connected in parallel is R6×Rth/(R6+Rth). By connecting the temperature sensing element Rth and the resistance R6 in parallel, the combined resistance linearly reduces in a desired temperature range as illustrated in FIG. 4.

A combined resistance of the temperature sensing element Rth, the resistance R6 and the resistance R8, that is, the combined resistance of the temperature sensing section 41 (the combined resistance of the temperature sensing section 41 will be hereinafter denoted by Rc) is expressed by expression (1). By connecting the resistance R8 in series to the temperature sensing element Rth and the resistance R6 which are connected in parallel, the combined resistance Rc reduces with a desired temperature coefficient (gradient) as illustrated in FIG. 4.

[Expression 1]

$$Rc = \frac{R6 \times Rth}{R6 + Rth} + R8 \tag{1}$$

Returning to FIG. 3, the amplifier 42 is configured by having a resistance R7 and an operational amplifier U2 in addition to the temperature sensing section 41. An output of the temperature sensing section 41 (an output of the resistance R8) is connected to an inverting input terminal of the operational amplifier U2. The reference voltage VREF is connected to a noninverting input terminal of the operational amplifier U2. An electric potential Vo that is outputted from an output terminal of the operational amplifier U2 is inputted to the inverting input terminal via the resistance R7. Further, the electric potential Vo outputted from the operational amplifier U2 is inputted to the ADC 33 of the position detection circuit 32 of the processor 3 through the cable 15 and the connector portion 16.

Figure 5:
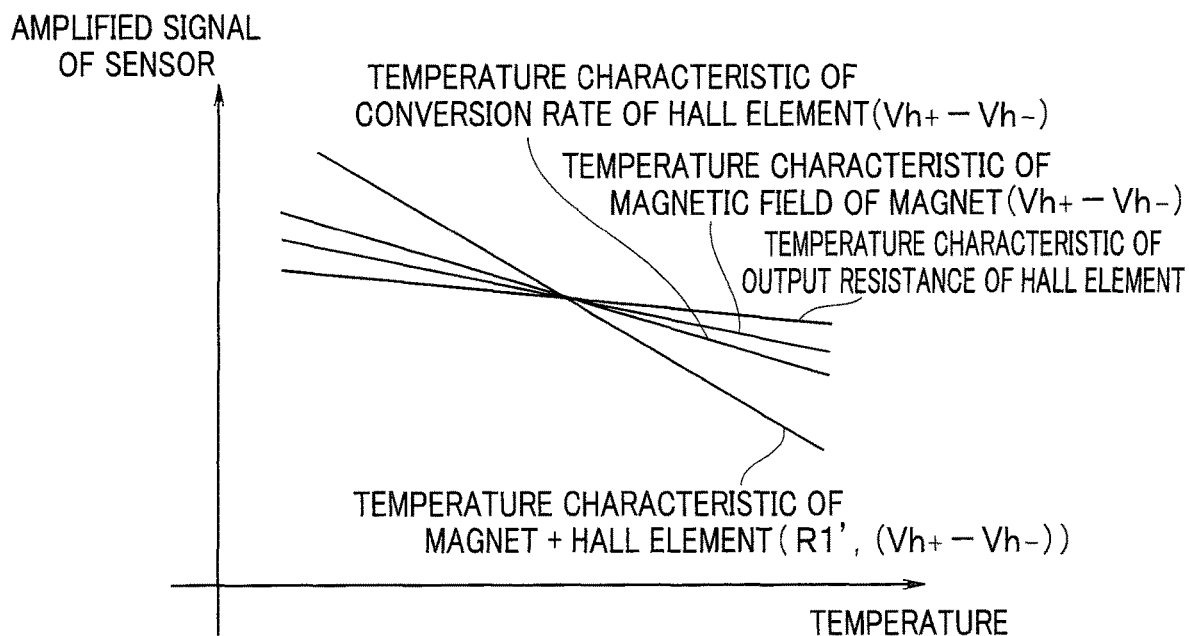
FIG. 5 is a diagram for explaining a relationship between an amplified signal of the sensor and a temperature.
Figure 6:
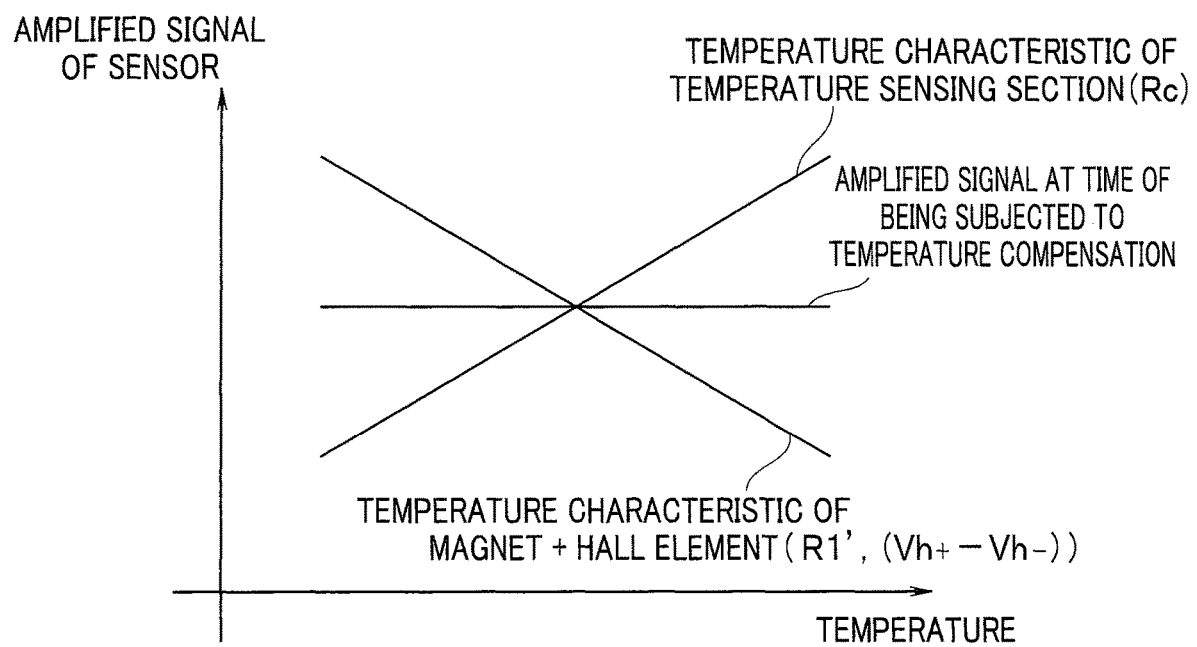
FIG. 6 is a diagram for explaining the relationship between the amplified signal of the sensor and the temperature.

Here, an amplified signal of the sensor 27, which is subjected to temperature compensation by the temperature sensing section 41, that is, the electric potential Vo that is outputted from the operational amplifier U2 will be described. FIG. 5 and FIG. 6 are diagrams for explaining a relationship between the amplified signal of the sensor and the temperature.

The electric potential Vo (amplified signal) which is outputted from the operational amplifier U2 is expressed by equation (2). Here, R1' represents a combined resistance of the resistance R1 and an output resistance $Rh_-$ of the sensor 27, and is expressed by equation (3). The combined resistance R1' changes in accordance with the temperature when the output resistance $Rh_-$ has a temperature coefficient.

Likewise, R2' represents a combined resistance of the resistance R2 and an output resistance $Rh_+$ of the sensor 27, and is expressed by equation (4). The combined resistance R2' changes in accordance with the temperature when the output resistance $Rh_+$ has a temperature coefficient.

Here, the resistances R1 to R4 of the differential amplifying section 40 are generally set to satisfy expression (5). Consequently, the electric potential Vo that is outputted from the operational amplifier U2 is finally determined by the combined resistance R1', the combined resistance Rc of the temperature sensing section 41, the resistance R3, the resistance R7, $(Vh_+ - Vh_-)$, and the reference voltage VREF as illustrated in expression (6). Note that $(Vh_+ - Vh_-)$ represents the output signal of the sensor 27.

[Expression 2]

$$Vo = -\frac{R7}{Rc} \times \frac{R3}{R1'}(Vh_+ - Vh_-) - \frac{R7}{Rc}\left(1 - \frac{R2'}{R1'} \times \frac{(R1' + R3)}{(R2' + R4)}\right)Vh_+ + VREF + \frac{R7}{Rc}\left(1 - \frac{R2'}{R1'} \times \frac{(R1' + R3)}{(R2' + R4)}\right)VREF \tag{2}$$

[Expression 3]

$$R1' = R1 + Rh_- \tag{3}$$

[Expression 4]

$$R2' = R2 + Rh_+ \tag{4}$$

[Expression 5]

$$\frac{R2'}{R1'} \times \frac{(R1'+R3)}{(R2'+R4)} \approx 1 \qquad (5)$$

[Expression 6]

$$Vo \approx -\frac{R7}{Rc} \times \frac{R3}{R1'}(Vh_+ - Vh_-) + VREF \qquad (6)$$

When the sensor 27 is the Hall element 27a, the output resistance Rh_ of the Hall element 27a has a positive temperature coefficient, so that when the temperature increases, the resistance also increases. In this case, the combined resistance R1' also has a positive temperature coefficient, so that the combined resistance R1' also increases when the temperature increases. As a result, the amplified signal of the sensor 27 reduces when the temperature increases (refer to a temperature characteristic of the output resistance of the Hall element in FIG. 5).

Further, when the sensor 27 is the Hall element 27a, the output signal of the sensor 27 (Vh_+-Vh_-) has a negative temperature coefficient, and therefore, reduces because the temperature increases. There are two factors to this. The first one is that the magnetic field of the magnet 26 has a negative temperature coefficient, and as the temperature rises, the magnetic field reduces (refer to a temperature characteristic of the magnetic field of the magnet in FIG. 5). The second one is that a conversion rate at which the magnetic field of the Hall element 27a is converted into a voltage has a negative temperature coefficient, and as the temperature increases, the conversion rate reduces (refer to a temperature characteristic of the conversion rate of the Hall element in FIG. 5).

In this way, when the sensor 27 is the Hall element 27a, three factors that are the output resistance Rh_ of the Hall element 27a, the magnetic field of the magnet 26 and the conversion rate of the Hall element 27a have temperature dependency. All of the three factors have such a characteristic that when the temperature increases, the amplified signal of the sensor 27 reduces. As a result, as shown in the temperature characteristic of the magnet+the Hall element in FIG. 5, the amplified signal of the sensor 27 reduces when the temperature increases.

The combined resistance Rc of the temperature sensing section 41 has a negative temperature coefficient, and when the temperature increases, the combined resistance Rc reduces, as illustrated in FIG. 4 described above. Consequently, the amplified signal of the sensor 27 increases when the temperature increases as illustrated in FIG. 6.

As illustrated in FIG. 6, by the temperature dependency of the output resistance Rh_ of the Hall element 27a, the magnetic field of the magnet 26, and the conversion rate of the Hall element 27a, the amplified signal of the sensor 27 reduces as the temperature increases. On the other hand, by the temperature dependency of the combined resistance Rc of the temperature sensing section 41, the amplified signal of the sensor 27 is increased as the temperature increases. As a result, the temperature compensation circuit 28 can output the amplified signal of the sensor 27, which does not depend on the temperature, namely, is subjected to temperature compensation.

In the present embodiment, an amplification factor of the operational amplifier U1 of the differential amplifying section 40 is made larger than an amplification factor of the operational amplifier U2 of the amplifier 42 in a subsequent stage. By making the amplification factor of the operational amplifier U1 in a preceding stage larger than the amplification factor of the operational amplifier U2 in the subsequent stage, performance of temperature compensation can be enhanced.

The temperature sensing element Rth and the resistance R6 are connected in parallel, and the resistance R8 is connected in series to the temperature sensing element Rth and the resistance R6 which are connected in parallel. The combined resistance of these temperature sensing element Rth, resistance R6 and resistance R8 changes linearly in accordance with the temperature, whereby the amplification factor of the signal changes linearly and temperature compensation is performed.

A parallel circuit portion of the temperature sensing element Rth and the resistance R6 is a circuit portion that adjusts the combined resistance so that the combined resistance changes linearly with respect to the temperature. The resistance R8 which is connected in series to the temperature sensing element Rth and the resistance R6 is a circuit portion that adjusts a change amount (the temperature coefficient) of the combined resistance to the temperature.

The temperature coefficient of the combined resistance of the temperature sensing element Rth, the resistance R6 and the resistance R8 is set so that a sum of a temperature coefficient of a conversion ratio from a detected physical quantity of the sensor 27 to a voltage, and a temperature coefficient of a differential amplification factor by temperature dependency of the sensor decreases. The temperature compensation circuit 28 thereby enables correction of temperature characteristics of the conversion ratio to the voltage of the sensor 27 and the output resistance of the sensor 27.

Further, when the sensor 27 is the Hall element 27a, the temperature coefficient of the combined resistance of the temperature sensing element Rth, the resistance R6 and the resistance R8 is set so that a sum of a temperature coefficient of a magnetic flux density of the magnet 26, a temperature coefficient of a conversion rate from a magnetic flux density of the Hall element 27a to a voltage, and a temperature coefficient of the differential amplification factor by the temperature dependency of the output resistance of the Hall element 27a decreases. Therefore, the temperature compensation circuit 28 enables correction of temperature characteristics of the magnet 26 and the Hall element 27a. The temperature compensation circuit 28 enables accurate temperature correction by correcting the temperature characteristics of the magnet 26 and the Hall element 27a.

As above, the endoscope 2 of the present embodiment is provided with the temperature compensation circuit 28 in the distal end portion 11, and performs temperature correction of the sensor 27 in the endoscope 2. Consequently, the processor 3 configured to be connected to the endoscope 2 does not have to have the function concerning temperature correction. As a result, it becomes easy for the endoscope 2 to ensure compatibility with processors of the previous generation or the next generation. Further, since temperature correction of the sensor 27 is performed in the endoscope 2, the processor 3 does not have to perform temperature correction corresponding to the kind of the endoscope 2 which is connected thereto, and processing load of the processor 3 does not increase.

Consequently, according to the endoscope of the present embodiment, it becomes possible to compensate temperature dependency of the sensor without performing temperature correction in the processor.

Second Embodiment

Next, a second embodiment will be described.

Figure 7:
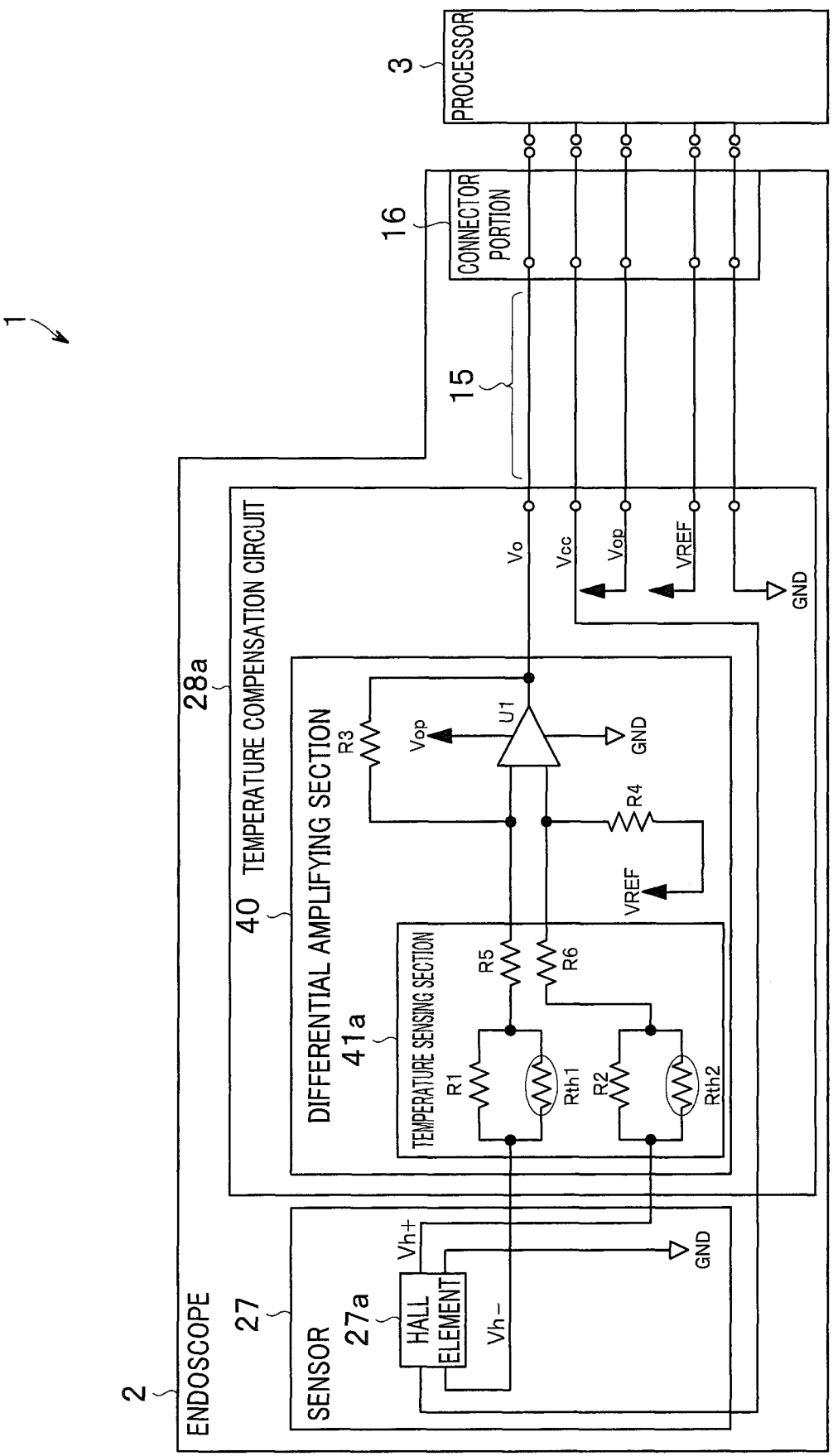
FIG. 7 is a diagram illustrating a detailed configuration of a temperature compensation circuit according to a second embodiment.

FIG. 7 is a diagram illustrating a detailed configuration of a temperature compensation circuit of the second embodiment. Note that in FIG. 7, the same components as in FIG. 3 will be assigned with the same reference signs and explanation of the components will be omitted.

The endoscope 2 of the second embodiment is configured by using a temperature compensation circuit 28a instead of the temperature compensation circuit 28 in FIG. 3. The temperature compensation circuit 28a has the differential amplifying section 40. The differential amplifying section 40 is configured by having a temperature sensing section 41a.

The temperature sensing section 41a has a circuit in which a resistance R5 is connected in series to a parallel connection portion of a temperature sensing element Rth1 and the resistance R1, and a circuit in which the resistance R6 is connected in series to a parallel connection portion of a temperature sensing element Rth2 and the resistance R2. The resistance R5 is connected to the inverting input terminal of the operational amplifier U1. Likewise, the resistance R6 is connected to the noninverting input terminal of the operational amplifier U1.

In this way, the temperature compensation circuit 28a is provided with the circuits including the temperature sensing elements Rth1 and Rth2 and performs temperature compensation to the respective two inputs of the operational amplifier U1 of the differential amplifying section 40. The other configuration is the same as the configuration of the first embodiment.

Here, an amplified signal of the sensor 27 subjected to temperature compensation by the temperature sensing section 41a, that is, the electric potential Vo that is outputted from the operational amplifier U1 will be described.

The electric potential Vo (amplified signal) outputted from the operational amplifier U1 is expressed by expression (7). Here, when a combined resistance of the temperature sensing element Rth1, the resistance R1 and the resistance R5 is set as Rc1, the combines resistance Rc1 is expressed by expression (8). Likewise, when a combined resistance of the temperature sensing element Rth2, the resistance R2, and the resistance R6 is set as Rc2, the combined resistance Rc2 is expressed by expression (9).

Rc1' represents a combined resistance of the combined resistance Rc1 and the output resistance $Rh_-$ of the sensor 27, and is expressed by expression (10). Likewise, Rc2' represents a combined resistance of the combined resistance Rc2 and the output resistance $Rh_+$ of the sensor 27, and is expressed by expression (11).

Here, the respective resistances of the temperature sensing section 41a are set so that combined resistance Rc1=combined resistance Rc2 is established, and thereby expression (12) is established. Therefore, the electric potential Vo outputted from the operational amplifier U1 is ultimately determined by the resistance R3, the combined resistance Rc1', $(Vh_+ - Vh_-)$ and the reference voltage VREF as shown by expression (13). Note that a temperature coefficient of the combined resistance Rc1 may be set in consideration of temperature coefficients of the output resistance $Rh_-$ of the Hall element 27a, the magnetic field of the magnet 26 and the conversion rate of the Hall element 27a, as in the first embodiment.

[Expression 7]
$$Vo = \frac{R3}{Rc1'}(Vh_+ - Vh_-) + \left(1 - \frac{Rc2'}{Rc1'} \times \frac{(Rc1' + R3)}{Rc2' + R4}\right)Vh_+ + \left(1 - \frac{Rc2'}{Rc1'} \times \frac{(Rc1' + R3)}{(Rc2' + R4)}\right)VREF \quad (7)$$

[Expression 8]
$$Rc1 = \frac{R1 \times Rth1}{R1 + Rth1} + R5 \quad (8)$$

[Expression 9]
$$Rc2 = \frac{R2 \times Rth2}{R2 + Rth2} + R6 \quad (9)$$

[Expression 10]
$$Rc1' = Rc1 + Rh_- \quad (10)$$

[Expression 11]
$$Rc2' = Rc2 + Rh_+ \quad (11)$$

[Expression 12]
$$\frac{Rc2'}{Rc1'} \times \frac{(Rc1' + R3)}{(Rc2' + R4)} \approx 1 \quad (12)$$

[Expression 13]
$$Vo \approx -\frac{R3}{Rc1'}(Vh_+ - Vh_-) + VREF \quad (13)$$

According to the configuration like this, in the temperature compensation circuit 28a of the endoscope 2 of the present embodiment, the amplifier 42 can be deleted with respect to the temperature compensation circuit 28 in FIG. 3, so that a circuit area can be made smaller than a circuit area of the temperature compensation circuit 28 of the first embodiment.

The present invention is not limited to the embodiments and modifications described above, but various changes, alterations and the like can be made within the range without changing the gist of the present invention.

What is claimed is:

1. An endoscope comprising:
   an insertion portion;
   a sensor arranged in a distal end portion of the insertion portion; and
   a temperature compensation circuit configured to perform temperature compensation of an output signal of the sensor, arranged in the distal end portion of the insertion portion,
   wherein the temperature compensation circuit comprises:
      an operational amplifier configured to amplify an output signal of the sensor; and
      a temperature sensing section comprising:
         a temperature sensing element and a first resistance connected in a parallel connection; and
         a second resistance connected in series to the parallel connection of the temperature sensing element and the first resistance.

2. The endoscope according to claim 1,
   wherein the operational amplifier is connected to an input portion of an amplifier, and
   wherein the amplifier comprises the temperature sensing section.

3. The endoscope according to claim 2,
wherein an amplification factor of the operational amplifier is larger than an amplification factor of the amplifier.

4. The endoscope according to claim 1,
wherein a combined resistance of the temperature sensing element and the first resistance changes in accordance with a temperature,
wherein the second resistance is configured to adjust a change amount of the combined resistance to the temperature, and
wherein the change amount is set so that a sum of:
   a temperature coefficient of a conversion ratio from a detected physical quantity of the sensor to a voltage; and
   a temperature coefficient of a differential amplification factor by temperature dependency of the sensor, decreases.

5. The endoscope according to claim 1, further comprising: a magnet wherein the sensor comprises a magnetoresistive element, wherein a combined resistance of the temperature sensing element and the first resistance changes in accordance with a temperature, wherein the second resistance is configured to adjust a change amount of the combined resistance to the temperature, and wherein the change amount is set so that a sum of: a temperature coefficient of a magnetic flux density of the magnet, a temperature coefficient of a conversion rate from a magnetic flux density of the magnetoresistive element to a voltage; and a temperature coefficient of a differential amplification factor by temperature dependency of an output resistance of the magnetoresistive element, decreases.

6. The endoscope according to claim 1,
wherein the temperature sensing element comprises a chip type negative temperature coefficient thermistor having a negative temperature coefficient.

7. An endoscope apparatus comprising:
the endoscope according to claim 1; and
a processor,
wherein the endoscope comprises:
   a cable; and
   a connector configured to be detachably connected to the processor, and
wherein the processor is configured to:
   generate a reference voltage that is supplied to the operational amplifier; and
   transmit the reference voltage through the connector and the cable.

8. An endoscope apparatus comprising:
the endoscope according to claim 1; and
a processor,
wherein the endoscope comprises:
   a cable; and
   a connector configured to be detachably connected to the processor, and
wherein the connector is configured to:
   generate a reference voltage that is supplied to the operational amplifier; and
   transmit the reference voltage through the cable.

* * * * *